United States Patent [19]

Loda

[11] 4,063,314
[45] Dec. 20, 1977

[54] TOTAL WRIST JOINT PROSTHESIS

[76] Inventor: Antonio Guillermo Loda, Galileo 2446, Buenos Aires, Argentina

[21] Appl. No.: 704,484

[22] Filed: July 12, 1976

[30] Foreign Application Priority Data

July 15, 1975 Argentina .............................. 259753
July 2, 1976 Argentina .............................. 263831

[51] Int. Cl.² .............................................. A61F 1/24
[52] U.S. Cl. .................................... 3/1.91; 128/92 C
[58] Field of Search ............................. 3/1, 1.9–1.913; 128/92 C, 92 CA

[56] References Cited

U.S. PATENT DOCUMENTS

| | | | |
|---|---|---|---|
| 3,760,427 | 9/1973 | Schultz | 3/1.91 |
| 3,795,922 | 3/1974 | Herbert et al. | 128/92 C |
| 3,837,008 | 9/1974 | Bahler et al. | 3/1.91 |
| 3,842,442 | 10/1974 | Kolbel | 3/1.91 |
| 3,909,853 | 10/1975 | Lennox | 3/1.91 |

OTHER PUBLICATIONS

Original Mueli Total Wrist, Advertisement by Promed International Inc., The Journal of Bone & Joint Surgery, vol. 55-A, No. 3, Apr. 1973.
McKee Finder Joints (No. 6949), Vitallium Surgical Appliances, (Catalog), Austenal Medical Div., Howmet Corp., New York, N. Y., p. 53.

Primary Examiner—Ronald L. Frinks

[57] ABSTRACT

A total wrist prosthesis of the type which is permanently included by surgery between the hand and the forearm with osteotomy of the carpus, comprising a stem having a section and length adequate for its nailing in the radial bone, a substantially rectangular plane base from one face of which said stem projects, a support arranged on the opposite face of said base displaced from the axial axis of said stem, a rotula articulated in said support, a second stem projecting in the opposite direction from said first stem connected with said rotula and nailable in the third metacarpal bone and in the capitate bone. In one variation a thin cylindrical stem projects from the neck of the second stem bent at an angle at a distance from said second stem to provide a substantially parallel sector to said second stem allowing rotational movement. In a second variation a pair of planar triangular transverse projections are arranged in the neck of the second stem symmetrically with respect to its axis, the projections having a side perpendicular to said axis and being nailable in the third metacarpal and in the body of the capitate bone.

6 Claims, 10 Drawing Figures

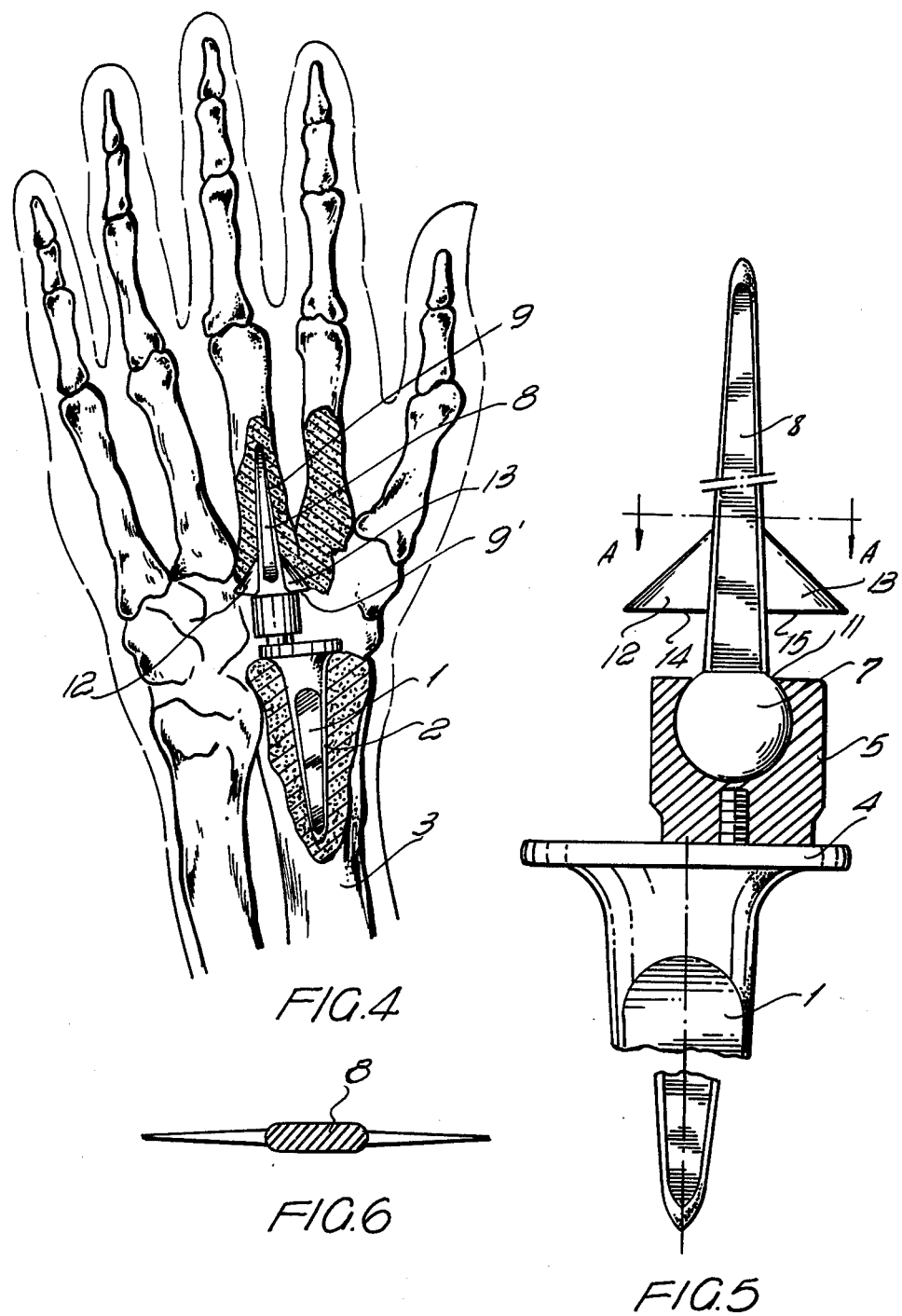

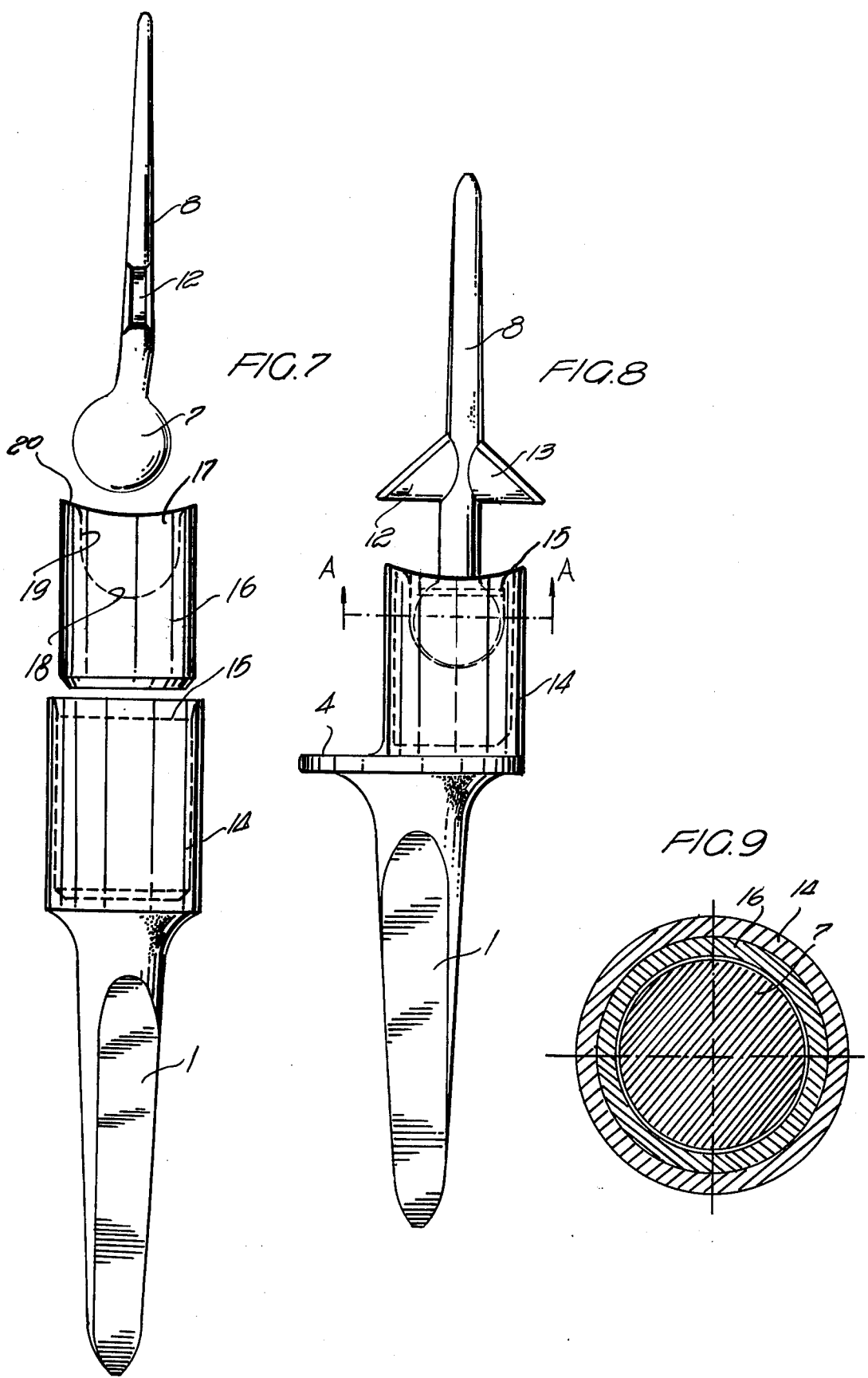

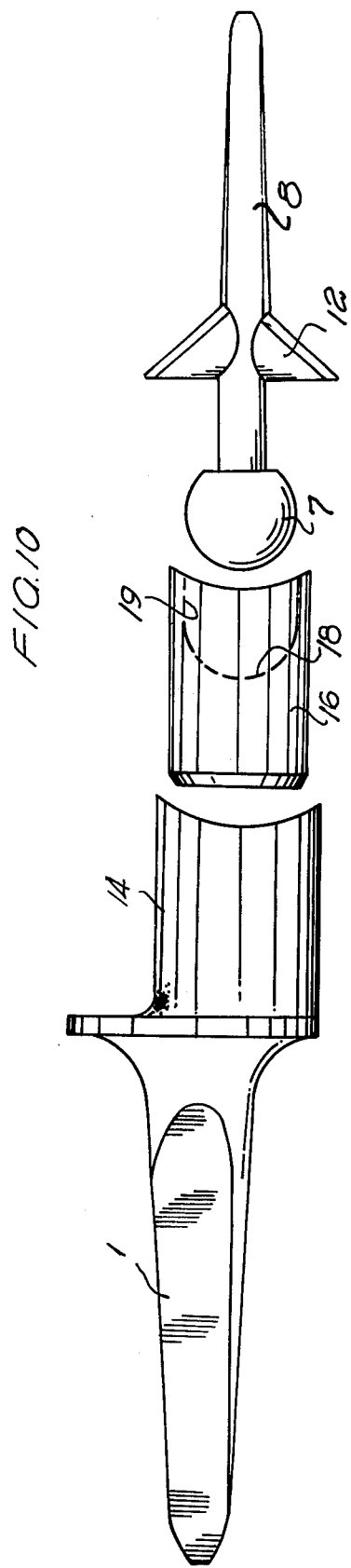

TOTAL WRIST JOINT PROSTHESIS

BACKGROUND OF THE INVENTION

This invention refers to a total prosthesis of the wrist. Up to now, no prosthesis is known to replace the wrist joint, similarly, the articulation of the wrist. When, as a result of accidents or more frequently owing to rheumatic infections, the carpus bones are wounded, among its eight small bones or between these and the radius and ulnar joint surfaces, or among these and the metacarpal bones of the hand, both, surgery and medicines have few possibilities to remedy the harm done.

Thus, the complex wrist osteoarthromuscular structure loses its major functions (flexion, extension and rotation) all of which are essential parts of the prehensile action of the hand. It is understandable that when the sickness is localized in the wrist, independent of the fingers, these may improve their function, if the wrist can regain its normal movement, and conversely, they may be affected in their function if the wrist remains rigid. This invention proposes a total wrist prosthesis placed between the radius distal end and the metacarpal bone corresponding to the middle finger. According to each case, one or several of the carpus small bones must be carved or excised. This operation does not bring any inconvenience because the wrist prosthesis mechanically replaces the four angular wrist movements as well as the circumduction movement. In other words, it is possible to make the wrist go back to its original movements.

SUMMARY OF THE INVENTION

The scope of the invention fully arises from the description given in the definition "Total wrist joint prosthesis ." This prosthesis belongs to the type grafted by means of joint surgery between the hand and the forearm, with partial osteotomy of the carpus, characterized by comprising a proximal stem fitted intramedullary by cementing in an axial hole formed in the radial bone. This stem is perpendicularly joined with a rectangular plane base, the opposite face of which is connected with a rotula or ball and socket joint, displaced from the axial axis of this stem. This system forms a proximal functional unit. Opposite to the first said distal stem, a stem is introduced into the medular canal of the large third metacarpal bone and into the body of the capitate bone. From the neck of this distal stem, a thin stem is projected. This stem can be bent, at a convenient distance, in order to provide a parallel stem to the distal stem, whose section and position allows the convenient limitation for the angular movement of the distal stem.

Summing up, the major aim of this invention is to provide a total wrist prosthesis formed by a ball and socket joint, from which stems are introduced in at least one of the metacarpal bones and the radial bone, opposed to each other. The distal stem is also an object of the present invention whereby a secondary stem is provided which by being also nailable in one of the metacarpal bones prevents the free rotation of the distal stem.

It constitutes another object of the invention to provide different limitations to the angular movement of said distal stem, as a consequence of the section of its neck and its position of attachment to said ball and socket joint or rotula.

It is a further object of the invention to arrange in replacement of the thin lateral secondary stem, a flap in the form of a transverse double projection where each projection possesses a substantially triangular perimeter with a side which is perpendicular to the axis of the distal stem. This flap gives the same results as the secondary thin stem, simplifying both the construction of the device and the surgical manuevering for its placement, since this avoids its insertion in the corresponding metacarpal bone. These projections offer the desired stability as they are inserted inside the body of the capitate bone.

Another object of the invention consists also in forming the coupling between the support of the ball and the joint socket and the plane base as single unit. The rectangular plane base and the support of the ball and joint socket form a tubular projection presenting an open cavity with an axis eccentric with respect to the distal stem, in which inside is attached a member of an elastomeric material, having an external surface concurrent with the internal surface of said cavity. This member having a receiving spherical cavity for the rotula is made of an elastomeric material, whereby it allows the ball to be well placed in its position inside the cavity, taking advantage of the resiliency of the elastomeric material. The latter is inserted in the tubular projection, with the assembly being integrated in this manner. The assembly can take advantage of the anti-frictional characteristics of the elastomeric material forming said member to improve the movement conditions of the articulation.

DESCRIPTION OF THE DRAWINGS

In order to get a clear idea of the nature of this invention, there is accompanied herewith a set of explanatory drawings, which illustrate a preferred embodiment. These drawings explain the best possible approach to an ideal device, but by no means are they restrictive of the true scope of the invention as contained in the claims accompanying this specification. Thus, there is the possibility of introducing "any type of modification" which does not alter the essence of what is claimed.

In said drawings, the same numerals designate the same parts, or similar ones.

FIG. 4 is a view of the skeleton of a hand and a portion of the forearm wherein a variation of the prosthesis according to the present invention has been applied.

FIG. 5 is a view in a greater scale of the variation of the prosthesis referred to in FIG. 4.

FIG 6 shows a section through line A—A of FIG. 5.

FIG. 7 is an exploded view of the elements constituting a second variation of the prosthesis according to the invention.

FIG. 8 is a view of a longitudinal section of the mounted assembly of the variation of FIG. 7.

FIG. 9 is a view of a longitudinal section through line A—A of FIG. 8.

FIG. 10 is a similar view which is illustrated in FIG. 7, showing another variation of the embodiment.

DETAILED DESCRIPTION

Figures 1, 2, 3:
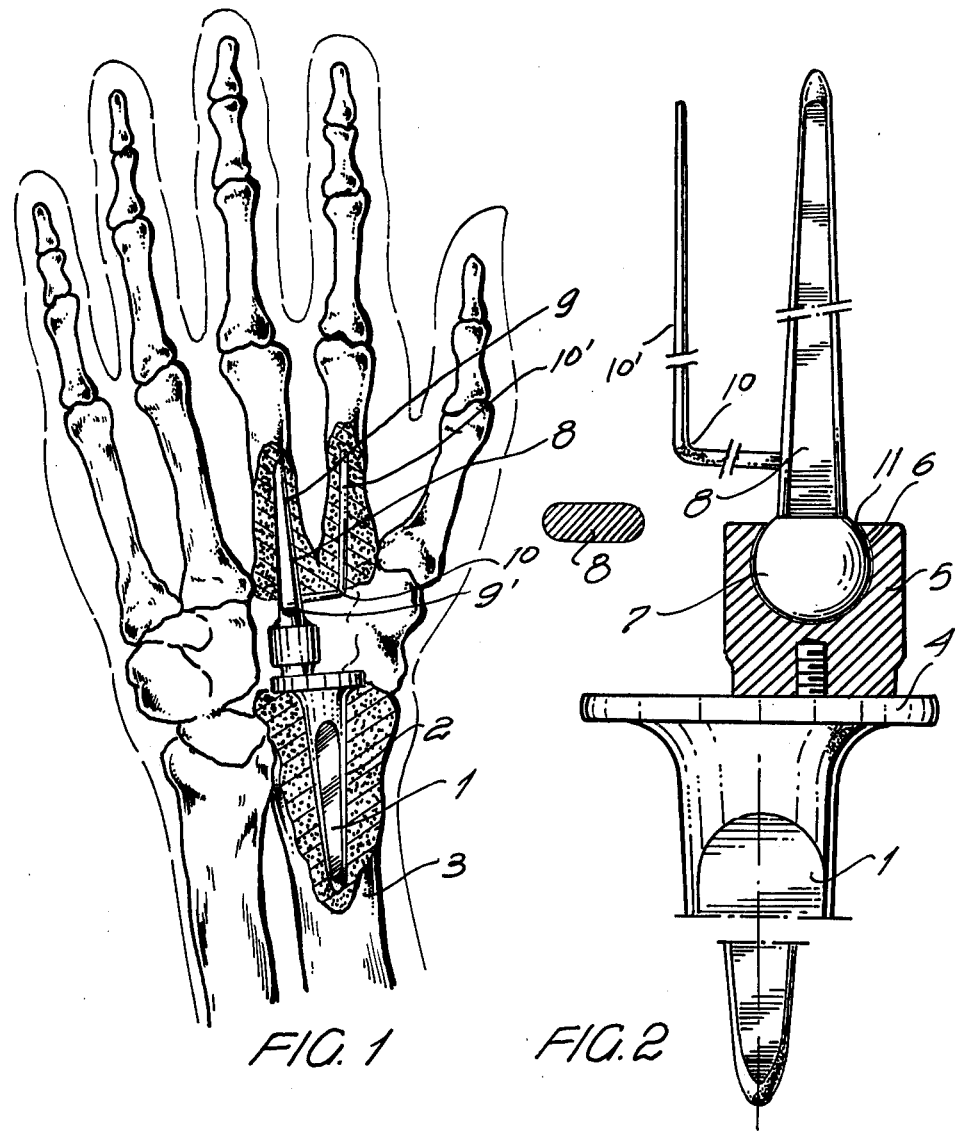
FIG. 1 shows the skeleton of a hand and a portion of the forearm wherein the prosthesis has been applied and is conveniently attached.
FIG. 2 shows said prosthesis in a greater scale.
FIG. 3 schematically shows the manner in which the limitations to the angular movements of the articulation are provided.

As illustrated in FIGS. 1 and 2, the mechanical prosthesis comprises essentially the main stem 1 whose section and length are adequate for its nailing and cementing inside the axial orifice 2 formed in the radial bone 3 of the forearm.

Said stem 1 is perpendicularly projected from the plane base 4 to which a support 5 is joined at the opposite side of the base which has a spherical cavity 6 wherein there is housed a "rotula" 7 and from which the distal stem 8 is projected in an opposite direction to the first stem 1. This stem 8 is acuminated having a rectangular section, enclosable in an opening 9 formed in the third metacarpal bone 9'. From the neck in said second stem 8 a secondary stem 10 is projected, as seen in the drawings, and at a certain distance this thin stem which is thinner than stem 8 is bent at an angle, which allows the arrangement of a sector 10' parallel to the stem 8.

The said rotula 7 need not necessarily be housed with a close fit in its support 5, since the contractions of tendons and muscles prevent by themselves its outward displacement. Since the natural movements of the hand with respect to the forearm, in its basic movements (flexion, extension and lateral) are not equal in their displacements, by regulating the neck width of the stem 8, its thickness and its position of projection from the rotula, axially coinciding with the center of the sphere or slightly displaced, the stops which in one or another direction are provided by the mouth 11 of the support 5 of the rotula will limit the angular movements as the case may be (see FIG. 3).

The support 5 will be displaced from the axial axis of the stem 1 as it is convenient to the positional relation to be determined by the size and situation of the axis of the 3rd metacarpal bone with respect to the axis of the radial bone. This requirement also regulates the space existing between the thinner stem 10' and the distal stem 8.

Once these proportional and size relationships are established and once the prosthesis is fitted in the way indicated in FIG. 1 by eliminating, carving or correcting the bones of the carpal which are deemed necessary, the wrist articulation will be mechanically restablished, since the prosthesis provides by itself the angular, rotatory movements for circumduction which are proper of the natural member. The prosthesis also provides the necessary stability to prevent a dislocation of the carpal bone. Referring now to FIGS. 4 to 6, the embodiment shown therein comprises a pair of projections 12 and 13 symmetrically arranged in relation to the distal stem 8. These projections extend transversely to the axis of the stem, in an essentially planar way with a triangular contour, with a side 14, respectively 15, perpendicular to the axis of the stem 8.

Preferably, the projections 12 and 13 have a decreasing thickness going from the stem to their extreme points and are inserted in the base of the orifice 9 of the metacarpal bone 9' which simplifies both the prosthesis manufacturing and the surgical maneuvering for its insertion. The function of the projections 12 and 13 performs the same work as the thin stem 10 to which reference was made when describing the arrangement of FIGS. 1 to 3. Referring to the embodiment shown in FIGS. 7 to 9, the support on base 4 is constituted by a tubular projection 14 which is monolithically projected from the rectangular plane base 4.

This tubular projection has an opening at its end 15 opposite to the rectangular plane base 4, the inside of the projection being preferably cylindrical, although this is not a critical configuration. An element 16, preferably cylindrical, but in any case with the same cross section as the tubular projection, is constructed by RCH 1000 polyethylene with some characteristics of resiliency, and thus is able to be inserted into the cavity of the projection.

This element 16 has formed in its inside a housing 17 with a hemispherical bottom 18 and a cylindrical side 19, limited by a slight inner edge 20, in which housing 17 it is possible to insert the "rotula" 7, which will be retained with a light pressure when the member 16 is inserted into the tubular projection 14 as shown in FIG. 8.

Since the material used to manufacture this element has good anti-frictional characteristics, the movement of the rotula 7 inside is greatly facilitated. Besides the resiliency of the material permits, as it was expressed above, an easy mounting of the assembly.

Referring now to the variation shown in FIG. 10, there is illustrated the spherical cavity 18 with its rotating axis which, corresponds to the center rotation of the rotula 7 housed therein. This center rotation is especially located eccentrically in respect to the axis of the main stem 1 and the axis of the distal stem 8, as observed in the figure.

This modification of the center rotation placement in the volar side, allows the increasing movement of the wrist.

Having thus described the present invention, and the way in which it has to be practiced, it is claimed as an exclusive property and right:

1. A total wrist prosthesis of the type which is permanently included by surgery between the hand and the forearm with osteotomy of the carpus, comprising a stem having a section and length adequate for its nailing in the radial bone, a substantially rectangular plane base from one face of which said stem projects, a support arranged on the opposite face of said base displaced from the axial axis of said stem, a rotula articulated in said support, a second stem projecting in the opposite direction from said first stem connected with said rotula and nailable in the third metacarpal bone and in the capitate bone, and a thin cylindrical stem projecting from the neck of said second stem bent at an angle at a convenient distance from said second stem so as to provide a substantially parallel sector to said second stem allowing rotational movement.

2. A total wrist prosthesis according to claim 1, wherein said second stem is acuminated with a substantially rectangular section, said support having a spherical cavity opening housing said rotula providing said second stem with different limitations to its angular displacement.

3. A total wrist prosthesis of the type which is permanently included by surgery between the hand and the forearm with osteotomy of the carpus, comprising a stem having a section and length adequate for its nailing in the radial bone, a substantially rectangular plane base from one face of which said stem projects, a support arranged on the opposite face of said base displaced from the axial axis of said stem, a rotula articulated in said support, a second stem projecting in the opposite direction from said first stem connected with said rotula and nailable in the third metacarpal bone and in the capitate bone, and a pair of transverse projections in the neck of said second stem arranged symmetrically with respect to the axis of said stem, said projections being substantially planar with a triangular contour and having a side perpendicular to said axis and being nailable in the third metacarpal and in the body of the capitate bone.

4. A total wrist prosthesis according to claim 3, wherein there is a coupling between the support of articulation for the rotula and the substantially rectangular plane base constituted by a tubular monolithic projection of said base having an open cavity, the axis of said tubular projection being eccentric with respect to the axis of said second stem, and an element attached inside of said tubular projection having an external surface concurrent with the internal surface of said cavity, said element being made of a plastic material and comprising a housing with a hemispherical bottom and a substantially cylindrical side wall and an edge slightly projected towards the axis of the housing wherein the rotula is inserted.

5. A total wrist prosthesis according to claim 4, wherein said element is made of polyethylene.

6. A total wrist prosthesis according to claim 3, wherein there is a volar displacement of the center of rotation of the rotula, said center of rotation being placed in the volar position in relation to the axis of the first and second stems which correspond to the radial and third metacarpal axis.

* * * * *